(12) United States Patent  
Kinev et al.

(10) Patent No.: US 9,709,551 B2  
(45) Date of Patent: Jul. 18, 2017

(54) METHOD FOR DETERMINING THE SENSITIVITY OF AN INDIVIDUAL TO LOW DOSE IONIZING RADIATION

(71) Applicant: Creative Scientist, Inc., Durham, NC (US)

(72) Inventors: Alexander V Kinev, Durham, NC (US); Dora Il'yasova, Greensboro, NC (US); Mark W. Dewhirst, Chapel Hill, NC (US)

(73) Assignee: Creative Scientist, Inc., Durham, NC (US)

( * ) Notice: Subject to any disclaimer, the term of this patent is extended or adjusted under 35 U.S.C. 154(b) by 0 days.

(21) Appl. No.: 14/764,409

(22) PCT Filed: Jan. 28, 2014

(86) PCT No.: PCT/US2014/013357  
§ 371 (c)(1),  
(2) Date: Jul. 29, 2015

(87) PCT Pub. No.: WO2014/120663  
PCT Pub. Date: Aug. 7, 2014

(65) Prior Publication Data  
US 2015/0355164 A1     Dec. 10, 2015

Related U.S. Application Data

(60) Provisional application No. 61/758,050, filed on Jan. 29, 2013.

(51) Int. Cl.  
G01N 33/50     (2006.01)  
A61B 6/00     (2006.01)  
A61B 6/03     (2006.01)

(52) U.S. Cl.  
CPC .......... *G01N 33/5005* (2013.01); *A61B 6/032* (2013.01); *A61B 6/542* (2013.01); *G01N 2800/52* (2013.01)

(58) Field of Classification Search  
CPC ..................................................... A61B 6/542  
See application file for complete search history.

(56) References Cited

U.S. PATENT DOCUMENTS

| | | |
|---|---|---|
| 6,475,490 B1 | 11/2002 | Srivastava et al. |
| 2003/0012793 A1 | 1/2003 | Srivastava et al. |
| 2005/0032726 A1 | 2/2005 | Li et al. |
| 2007/0086942 A1 | 4/2007 | Chang et al. |
| 2007/0098735 A1 | 5/2007 | Chandawarkar |
| 2007/0293458 A1 | 12/2007 | Shamsuddin et al. |
| 2009/0042991 A1 | 2/2009 | Barsoum et al. |
| 2009/0275884 A1 | 11/2009 | McNulty et al. |
| 2010/0049180 A1 | 2/2010 | Wells et al. |
| 2010/0068804 A1 | 3/2010 | Chute |
| 2010/0204093 A1 | 8/2010 | Kaushal et al. |
| 2011/0135641 A1 | 6/2011 | Isenberg et al. |

FOREIGN PATENT DOCUMENTS

| | | |
|---|---|---|
| EP | 969100 A1 | 1/2001 |
| EP | 2207595 A2 | 7/2010 |
| WO | 9805760 A2 | 2/1998 |
| WO | 0023093 A1 | 4/2000 |
| WO | 2006113572 A1 | 10/2006 |
| WO | 2007050978 A2 | 5/2007 |
| WO | 2008013985 A9 | 1/2008 |
| WO | 2009088550 A2 | 7/2009 |
| WO | 2009134967 A2 | 11/2009 |
| WO | 2010037402 A1 | 4/2010 |

OTHER PUBLICATIONS

Soule et al. The J of Immunology, 2007, 179:3276-3286.*  
Liang et al. J. Radiat. Res., 2011, 52:380-386.*  
PCT Written Opinion and Search Report of the International Searching Authority for International Application No. PCT/US2014/13357, International Filing Date Jan. 28, 2014.

* cited by examiner

*Primary Examiner* — Bin Shen  
(74) *Attorney, Agent, or Firm* — James G. Passé; Passé Intellectual Property, LLC

(57) ABSTRACT

The present invention relates to the innovation that ECFCs are a predictor of the likely result to the exposure of a patient to low dose ionizing radiation by comparing the results of exposure of cells to individuals already exposed to ECFCs.

5 Claims, 1 Drawing Sheet

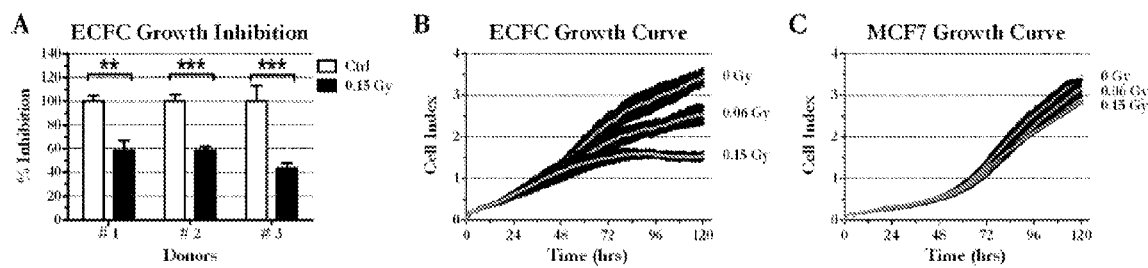

METHOD FOR DETERMINING THE SENSITIVITY OF AN INDIVIDUAL TO LOW DOSE IONIZING RADIATION

This application claims priority to U.S. provisional application No. 61/758,050 filed on Jan. 29, 2013 which is incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to the field of determining the sensitivity of an individual to a toxicant. In particular, it relates to the method of determining the sensitivity of an individual to low-dose ionizing radiation.

Description of Related Art

Ionizing radiation is an established human carcinogen. The widespread use of advanced radiological imaging, such as X-ray computed tomography scans (CT-scans), raises a concern about the potential danger of exposure to low-dose ionizing radiation (LDIR). Humans are likely to have variable responses to LDIR and therefore, medical exposure to LDIR may produce different effects depending on individual predisposition. For example, a familial history of cancer has been identified as a modifying factor of cancer risk associated with diagnostic radiation response. However, quantitative measures of an individual response to LDIR have not been developed. Studying the variability of responses to LDIR in human population or specific sub-groups cannot be done by direct experimentation. Therefore, donor-derived substances (body fluids, genetic material, or cells) have been used to gain an understanding on what predisposes a person to radiation-related diseases. Traditionally, peripheral blood lymphocytes have been used to study the differences in individual responses to ionizing radiation and LDIR in particular. These studies confirmed that individuals differ in their response to LDIR. However, the utility of these findings is hampered by low-proliferation potential of the primary lymphocyte cultures, low signal-to-noise ratio, and transience of the measured response indicators, such as DNA-damage response or oxidative stress.

Despite the alarming findings that LDIR from medical procedures increases the risk of various cancers, medical LDIR exposure in the U.S. remains one of the most prevalent risk factors for cancer, especially breast cancer. Such an exposure to LDIR has increased in the U.S. significantly due to the recent wide spread use of CT-scans. CT-scans are within the range of low-dose (i.e., <0.5 Gy) but involve much greater (in an order of magnitude) ionizing radiation doses as compared to other X-ray procedures. Accordingly, the carcinogenic risk posed by CT-scans may be significant. For example, it has been estimated that approximately 29,000 cancers could be related to CT-scans performed in the U.S. during the year of 2007 alone. In fact, the majority of these cases, i.e. two-thirds, were projected to occur in women based on higher frequency of CT-scans among women and the high risk associated with breast cancer. Other harmful effects of LDIR include increased risk of circulatory, respiratory, and digestive diseases. Thus, CT-scans currently present an important risk factor for cancer and several non-cancer outcomes.

Endothelial colony forming cells, or ECFCs, are a type of progenitor cell that was first identified by Ashahara and colleagues as mononuclear peripheral blood fraction-derived CD34-positive and CD45-negative cells that form colonies in cell culture. The main feature of ECFC is their visible appearance in a culture dish as single colonies of cobblestone-looking cells. ECFCs are called "late outgrowth endothelial cells" because they "appear" 1-3 weeks after the initial seeding on a culture dish of either a whole blood or mononuclear cell fraction of the blood. The most important features identified by the researchers in the field are the robust clonal growth and expression of a variety of cell surface markers characteristic to arterial and venous endothelial cells, and a restriction to the endothelial lineage during differentiation. In addition, ECFCs form capillary-like structures in vitro and capillary plexus in collagen, type I (plus fibronectin) gel plugs implanted in immunodeficient mice. Overall, ECFCs appear to display properties characteristic to endothelial progenitor cells.

Mesenchymal stem cells (MSC) are multipotent progenitor cells that can be isolated from adult bone marrow and can be induced in vitro and in vivo to differentiate into a variety of mesenchymal tissues, including bone, cartilage, tendon, fat, and muscle. It has been proposed that a cell can be classified as an MSC if it shows plastic adherent properties under normal culture conditions and has a fibroblast-like morphology and can undergo osteogenic, adipogenic and chondrogenic differentiation ex-vivo. Nevertheless, the cultured MSCs, like ECFCs express on their surface CD34, CD73, CD90 and CD105, while both cell types lack the expression of most lineage-specific markers.

It would be useful therefore to have a means for the determination of the risk of an individual to the exposure to LDIR in a given individual especially in a clinical setting. If a person was determined more sensitive, the individual could in combination with their doctor determine the risk of using CT-scans or other procedures involving LDIR or the like.

BRIEF SUMMARY OF THE INVENTION

The present invention relates to the discovery that if progenitor cells such as Endothelial Colony-Forming Cells (ECFCs) are isolated from an individual and the effects of LDIR on the cells are observed by studying the viability, proliferation and/or differentiation of the cells, the effect of such radiation on the individual can be predicted. In other words, the response of individual's progenitor cells to LDIR can be used as a predictor of how sensitive a particular individual (patient) will be to radiation. Diseases associated with LDIR are exemplified but not limited to cancer or cardiovascular disease.

Accordingly in one embodiment of the present invention there is a method of determining a patient's sensitivity to the exposure to low dose ionizing radiation (LDIR) comprising:
a) providing a database of information compiled by the method comprising:
   i. isolating and growing progenitor cells from each of a plurality of individuals;
   ii. exposing each of the individual's isolated cells to LDIR;
   iii. evaluating the effect of the LDIR on each of the isolated individual's cells by determining for each of the isolated individual's cells at least one of the change in at least one of the group comprising viability, proliferation and differentiation; and iv. arranging the evaluations from a lowest effect to highest effect to produce a range wherein the highest effect correlates with those individuals most sensitive to LDIR and the lowest effect with those individuals least sensitive to LDIR.

b) isolating and growing progenitor cells from the patient;

c) exposing the patient cells to LDIR;

d) evaluating the effect of the LDIR on the isolated patient cells by measuring the change in at least one of the group comprising viability, proliferation and differentiation of the patient cells; and e) comparing the results of the patient's cells evaluation with the evaluation arrangement in the database to determine which of the plurality of individuals results is most like the patient's.

f) advising the patient of their sensitivity to LDIR based on the comparison.

In another embodiment, the invention relates to a method of determining the sensitivity in a patient to the exposure of the patient to LDIR relative to a group of individuals prior to exposure of the patient to LDIR comprising comparing the effects of LDIR on the patients progenitor cells to the effects on the group of individuals progenitor cells who have been exposed to LDIR and whose progenitor cells produce a similar effect as the patient when exposed to LDIR and determining that the sensitivity to LDIR of the patient will be relatively similar to the group as the individual with a similar effect.

BRIEF DESCRIPTION OF THE DRAWINGS

FIGS. 1 a, b and c show the result of the relationship of LDIR exposure to ECFCs proliferation.

DETAILED DESCRIPTION OF THE INVENTION

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

DEFINITIONS

The terms "about" and "essentially" mean±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "determining" refers to the process of scientifically measuring the results of a particular activity as it relates to individual patients and the like. It assumes one skilled in the art will be making tests within that skill to observe and measure thing such as toxicological effects of either a patient or particular type of cell.

As used herein the term "toxicological effect" refers to the result in a patient or individual or on progenitor cells induced in both instances by the exposure to LDIR. In the case of a patient, it refers to the negative effect of a single or accumulated exposure to LDIR over time. It can be at a given dose, various doses or accumulated doses. Cancers are the most common type of result of exposure to LDIR so sensitivity to LDIR would help prevent cancer where one were known to be sensitive to LDIR. The toxicological effect on progenitor cells refers to a measured change in viability, proliferation and/or differentiation of the cells. In some cases, of course, the answer may be no change but any change based on the exposure to the radiation is noted for correlation to the effect of the same type of radiation on the individual patient or the like exposed to the same radiation as a single or multiple dose. That is, it is a predictor of the likely sensitivity of the individual exposure to LDIR and can be used to determine safe expose for the individual rather than using averages doses for the population as a whole.

As used herein, the term "patient" refers to a human or other mammal who is being tested for susceptibility or sensitivity to the effects of low dose ionizing radiation. The patient can be someone who is about to be exposed to LDIR for the purpose of a test (e.g. CT scan) or the like or can be done just for future information to make decisions about the safety of exposure to radiation of the patient.

As used herein the term "individual" refers to people or animals from whom a data base is being collected to determine the effect of low dose ionizing radiation on their progenitor cells and correlating it to the effect of the exposure to LDIR on the individual as a whole to create predictive information so that a patient with unknown reaction to the radiation can be correlated and predict the effect of radiation thereon. By comparing the sensitivity to a group of individuals as a whole, the group of individuals can be a general population or a specific group segregated by sex (male, female) or age (young, elderly, etc).

As used herein the term "exposure to LDIR" refers to the type of exposure an individual frequently encounters in routine medical treatments such as a CT scan and other general sources of LDIR one encounters in life. So both artificial and purposely induced exposure is intended. For testing it can be a single dose, repeated doses or doses of various intensities.

As used herein the term "database of information" refers to a collection of information about individuals. The information includes the effect that LDIR has on their progenitor cells, i.e. a collection of information relating to the correlation between the variety of responses possible with exposure to the organism. The collection of information can be held in any manner for example in a computer database in resident memory or can be a chart or other collection of information that can be utilized for comparison. The purpose is to provide a collection of many individuals and the result of exposure of cells and the result it has so when a patient who is not in the database is encountered their cells can be exposed and one can then look in the database to determine what the likely sensitivity relative to the database is based on how the cells react. The database can be arranged as a general population or by sex or age or the like.

The database comprises first collecting a plurality of individuals. Then progenitor cells are isolated from those individuals and grown up until enough to be tested is collected and then they are exposed to low dose ionizing radiation wherein the toxicological effect on the cells (i.e. change in viability, proliferation and or differentiation of the cells) is collected. The group is then evaluated from the highest effect (greatest change) to lowest effect (least change). The greater the change in progenitor cells the greater the sensitivity to LDIR.

As used herein the term "comparing the results" refers to taking the toxicological results of the patients progenitor cells being exposed to LDIR and looking in the database for individuals who had the same result when their cells were similarly exposed. Then by looking at the result that person had with exposed to LDIR one can determine the relative results to the group as a whole is likely with the patient. In one embodiment this can be accomplished by establishing, based on the size of the database, a relative likelihood of sensitivity to LDIR based on accumulating data. The more data the more accurate to the sensitivity (i.e. more individuals).

As used herein the term "dose" refers to the administration of ionizing radiation from a procedure or naturally occurring but in general refers to a low dose of less than about 0.5 Gy but in general at any level desired that is less than the 0.5 Gy, greater than about 0.0 Gy (in one embodiment greater than about 0.06 Gy).

As used herein the term "breast cancer" refers to breast cancer the result of exposure to LDIR and not other forms of breast cancer. Other toxicological effect or exposure to LDIR are known and can be discovered once one understands that the progenitor cells are predictive of whole organism exposure to LDIR.

As used herein the term "ECFC" refers to the generally accepted endothelial colony forming cells which are a type of progenitor cells.

Now referring to the drawings, FIGS. 1 a, b and c show the result of the relationship between LDIR and progenitor cells (ECFCs) proliferation. ECFCs growth is sensitive to LDIR, whereas immortalized cells (MCF7 breast cancer cell line) are not. (A) Growth inhibition in response to a single radiation dose of 0.15 Gy is consistently observed in ECFCs isolated from three donors. (B) Growth inhibition response of ECFCs from Donor 2 to different doses of radiation. (C) Lack of response to low doses of radiation in MCF7 cell line.

EXPERIMENTAL

Endothelial Colony-Forming Cells Exhibit Robust Growth in Vitro

ECFCs were isolated from mononuclear cells fractions of 3 cord blood samples designated as CB002, CB005, and CB006. The colony-forming cells could be identified under a microscope as early as 5 days after the plating of mononuclear cells on collagen-coated dishes. Well-developed colonies appeared between days 9 and 12. Cells within the colonies exhibited a "cobblestone" morphology, typical for endothelial cells, and were positive for the endothelial cell marker CD31. Based on a FACScan analysis, the isolated cells were highly positive for CD34 and negative for CD133/1 and CD133/2 (data not shown). ECFCs were also positive for other markers associated with endothelial cells, i.e. CD105 and CD73, and negative for markers characteristic to other blood cell lineages, i.e. CD2, CD 4, CD11 B, CD14, CD15, CD19, CD 45, CD56, and CD90. Additional indicators of endothelial phenotype included the formation of a capillary-like network in Matrigel, absorption of Ulex lectin, and uptake of acetylated LDL (data not shown). Individual donor samples produced a variable number of colonies with CB002, CB005, and CB006 giving rise to 30, 45, and 3 colonies, respectively, which corresponded to $1.9 \times 10^6$, $1.1 \times 10^6$, and $6 \times 10^4$ of cells. The colonies from each donor were pooled, passaged 2 or 3 times, and frozen in aliquots until further use. After thawing, cell viability was 92-98% based on the trypan blue exclusion method. Cryopreservation of up to 12 months did not affect ECFC proliferation capacity and cells demonstrated a robust growth in standard cell culture conditions. Based on our data, 1 million of ECFCs can yield as many as 10 billion cells after 1 month of expansion in optimized cell culture conditions.

Low-Dose Ionizing Radiation Produces a Cytostatic Effect in Actively Growing ECFC Cultures A real-time cell culture impedance measurement was used to monitor the effect of LDIR on ECFCs growth and proliferation. In actively growing cell cultures, the change of impedance correlates with the change in cell number (12). CB002, CB005, and CB006 ECFCs were seeded in quadruplicates in 96-well E-plates at 2000 cells per well and then either subjected to a single radiation dose of 0.2 Gy (18.28+/−0.3 Gy/min) or left untreated. The cells continued to grow for up to 72 hours without media change. Within the next 48 hours, all 3 non-irradiated ECFC cultures demonstrated close to a linear growth curve with an average cell population doubling time of 19.5±0.1 hours at 24 hours. Irradiated ECFC cultures initially grew at a rate comparable to the control cells with a mean population doubling time of 17.3±3.5 hours at 24 hours. However, at 48 hours, irradiated ECFCs grew considerably slower than the control cells; mean population doubling times were 38.7±3.5 in the irradiated cultures and 25.1±2.0 hours in the controls. By the 72-hour time point, the irradiated cultures from all 3 donors had significantly lower cells indexes compared to the untreated cultures (p-values for t-tests <0.05), indicating lower cell numbers.

To determine whether the observed growth inhibition was a result of radiation-induced cell death, a dead/live cell viability assay was employed. The assay revealed that at 72 hours, the ratio of dead/live cells did not increase in the irradiated cultures as compared to the non-irradiated cultures, suggesting that at 0.2 Gy, X-rays were not cytotoxic to ECFCs. LDH activity measurements produced similar results, i.e. the ratio of LDH activity in conditioned media to intracellular LDH activity did not increase after irradiation (data not shown). Together these data indicate that a single dose of LDIR inhibited the growth of ECFC cultures without causing cell death.

Cell growth inhibition by different LDIR doses was analyzed using CB005 ECFCs. To ensure linearity of cell growth during a longer period, cells were plated at a lower initial density (1000 cells/well). ECFCs were exposed to either a single dose of 0.06, 0.15, or 0.38 Gy or left untreated (control) and continued to grow for up to 72 hours. The initial cell growth rate of the irradiated cultures was similar to the untreated ones as demonstrated by growth curve [FIG. 3 (A)] and doubling time graphs. The population doubling time was 15.2±1.3 hours at the 24-hour time point in both control and irradiated cells. However, during the next 24 hours the growth of the irradiated cells was considerably impaired. By the 50-hour time point, the population doubling time was 24.7±2.6, 34.9±1.7, 40.6±4.3, and 49.2±5.4 hours in control and cultures irradiated with 0.06, 0.15, and 0.38 Gy, respectively. A WST-8 (cell counting) assay further confirmed these observations, demonstrating that the relative amounts of viable cells were lower in the irradiated cell cultures as compared to controls. Further, LDH activity in the media was used as an indirect measure to assess ECFCs death in response to X-rays. The release of intracellular enzyme LDH into culture medium can serve as an indicator of cell membrane damage associated with cell death. In this experiment, cells were irradiated with low (0.15 and 0.38 Gy) and high (2 Gy) radiation doses. LDH activity in the media was determined at 72 hours [FIG. 3 (D) (68 hours post-irradiation)]. There was no difference in LDH activity in media conditioned by irradiated vs. control cells, suggesting that low and as high as 2 Gy doses are not cytotoxic to ECFCs (p-values for t-test >0.05).

DISCUSSION

Our main finding was the observation of a protracted response of ECFCs to a single radiation at a dose as low as 0.06 Gy. ECFCs used in our experiments had typical endothelial cells morphology and surface markers and produced primary cultures with high proliferative potential. The ECFC proliferative potential was not significantly affected by long-term cryopreservation. These unique qualities of ECFCs are important for the logistics of studies dealing with sample collection from human subjects. In epidemiological studies, biospecimen collection depends on availability of study subjects and cannot be easily synchronized. Ability to store ECFCs samples insures feasibility of using ECFC-based assays in human studies.

Measurements of cell population growth in ECFC primary cultures demonstrated responsiveness of these cells to 0.2 Gy LDIR observed as a protracted deceleration of cell growth. The experiments with lower doses (0.06 and 0.15 Gy) confirmed responsiveness of ECFCs to LDIR at doses comparable to those produced by CT-scans (2, 13). The observed deceleration of cell growth in response to a single LDIR dose persisted for days, as opposed transient character of the DNA damage response measured by gamma-H2AX foci (within minutes).

Although our results did not completely exclude radiation-induced cell death, there are several indications that the observed differences reflect an inhibition of cell growth. Three endpoint assays convincingly demonstrated the lack of cell damage after 3 days of cell culture: cell-associated protease activity (dead/live cell ratio), intracellular dehydrogenase mediated conversion of WST-8 into formazan, and LDH activity in conditioned media. In addition, microscopic examination did not reveal any sign of cell damage or apoptosis for up to 1 week after irradiation.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed:

1. A method of determining a patient's of a selected species sensitivity to damage by the exposure of the patient to low dose ionizing radiation (LDIR) comprising:
   a) isolating and growing progenitor cells in vitro from each of a plurality of individuals of the same species as the patient;
   b) exposing each of the individual's isolated and grown cells to the same one or more dose of LDIR;
   c) evaluating the effect of the same one or more dose of LDIR on each of the isolated individual's cells by determining for each of the isolated individual's cells at least one of the change in at least one of the group consisting of proliferation and differentiation;
   d) arranging the evaluations from a lowest effect to highest effect on each individual to produce a range wherein the highest effect correlates with those individuals most sensitive to LDIR and the lowest effect with those individuals least sensitive to LDIR;
   e) collecting the evaluations in a database;
   f) isolating and growing progenitor cells from the patient;
   g) exposing the isolated and grown patient cells to the same one or more dose of LDIR as the individuals on the database;
   h) evaluating the effect of the LDIR on the isolated patient cells by measuring the change in at least one of the group consisting of proliferation and differentiation of the patient cells;
   i) comparing the results of the patient cell evaluation with the evaluation arrangement in the database to determine which of the plurality of individual's result is most like the patient's; and
   j) advising the patient of their sensitivity to LDIR based on the comparison wherein the more like other individuals who are more sensitive, the more sensitive they will be to the effect of LDIR.

2. The method according to claim 1 wherein the progenitor cells are endothelial colony forming progenitor cells (ECFC).

3. The method according to claim 1 wherein the plurality of individuals have a commonality selected from the group consisting of at least one of sex and age.

4. The method according to claim 1 wherein the low dose ionizing radiation is at least at a dose greater than 0.0 Gy to less than about 0.5 Gy.

5. The method according to claim 1 wherein the species is Homo sapiens.

\* \* \* \* \*